United States Patent [19]

Van Wezel et al.

[11] Patent Number: 4,946,676
[45] Date of Patent: Aug. 7, 1990

[54] VACCINE COMPRISING AN IMMUNOGENIC PROTEIN AND, AS AN ADJUVANT, A SUBSTANTIALLY NON-IMMUNOGENIC, SEQUENTIALLY HOMOLOGOUS PEPTIDE

[75] Inventors: Antonius L. Van Wezel, Bilthoven; Antonius G. Hazendonk, Nieuwegein; Eduard C. Beuvery, Vianen, all of Netherlands

[73] Assignee: De Staat Der Nederlanden, Leidschendam, Netherlands

[21] Appl. No.: 900,739

[22] Filed: Aug. 27, 1986

[51] Int. Cl.$^5$ ......................... A61K 39/12; C12N 7/04
[52] U.S. Cl. ......................................... 424/89; 424/86; 424/88; 424/93; 435/235; 435/236; 435/237
[58] Field of Search ....................... 424/89, 86, 93, 88; 435/235, 236, 237

[56] References Cited

PUBLICATIONS

Van Wezel et al., "New Approach to the Production of Concentrated and Purified Inactivated Polio and Rabies Tissue Culture Vaccines", 15th. IABS Congress, Develop. Biol. Standard, vol. 41, pp. 159–168, (S. Karger, Basel, 1978).
Van Wezel et al., "Inactivated Poliovirus Vaccine: Current Production Methods and New Developments", Reviews of Infectious Diseases, vol. 6, supplement 2, pp. S335–S340, 1984.
Embo J., 4, (1985), pp. 3339–3343.
Dev. Biol. Stand., 55, (1984), pp. 209–215.
Nature, 304, (1983), pp. 699–703.
Science, 229, (1985), pp. 1358–1365.
Nature, 291 (1981), pp. 547–553.
J. Mol. Biol., 174, (1984), pp. 561–585.
Proc. Natl. Acad. Sci. U.S.A., 81, (1984), pp. 1539–1543.
Proc. Natl. Acad. Sci. U.S.A., 82, (1985), pp. 2627–2631.
Nucl. Ac. Res., 13, (1985), pp. 2111–2125.
Proc. Natl. Acad. Sci. U.S.A., 82, (1985), pp. 732–736.
Vir. Res., 3, (1985), pp. 263–270.
Nucl. Ac. Res., 12, (1984), pp. 2969–2985.
Gene, 17, (1982), pp. 153–161.
Nucl. Ac. Res., 12, (1984), pp. 6587–6601.
Virology, 140, (1985), pp. 13–20.
Nature, 301, (1983), pp. 674–679.
J. Virol., 57, (1986), pp. 246–257.
Develop. Biol. Stand., 41, (1978), pp. 159–168.
Rev. Inf. Dis., 6, (1984), pp. 335–340.
Anal. Biochem., 83, pp. 346–356, (1977).
Virology, 130, pp. 243–246, (1983).
Nature, 227, pp. 680–685, (1970).
Proc. Natl. Acad. Sci. U.S.A., 76, pp. 4350–4354, (1979).
Vaccine, 1, pp. 17–22, (1983).

Primary Examiner—Margaret Moskowitz
Assistant Examiner—Abdel A. Mohamed
Attorney, Agent, or Firm—Brumbaugh, Graves et al.

[57] ABSTRACT

The invention relates to a new vaccine comprising a native protein capable of inducing the production of protective antibodies in a host, together with an adjuvant amount of certain proteins or peptides which, as such, are not capable of inducing substantial protective antibody titres but considerably enhance the immunizing activity of said native protein.

The amino acid sequences of the adjuvant proteins and peptides show homology with the native proteins. Combination of inactivated picornavirus, such as poliovirus, with adjuvant amounts of denatured picornavirus, such as poliovirus, capsis proteins, in a vaccine, is highly advantageous.

11 Claims, 1 Drawing Sheet

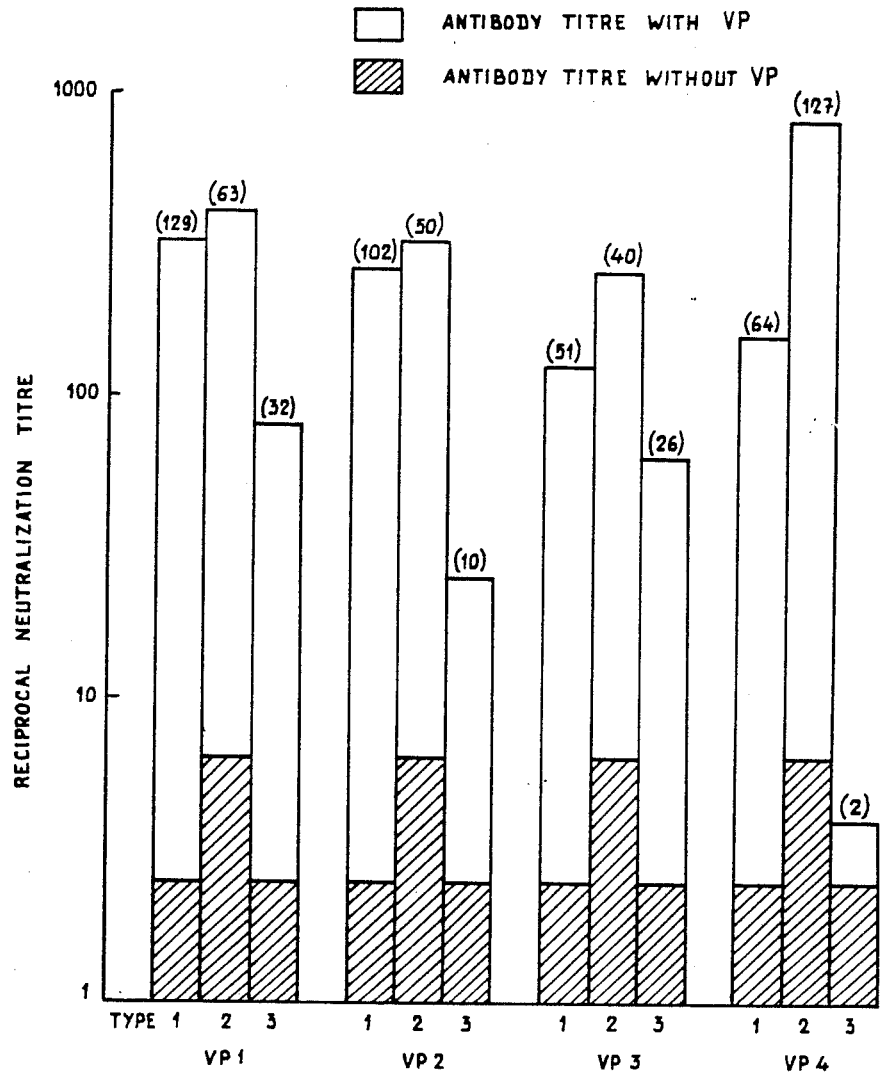

VACCINE COMPRISING AN IMMUNOGENIC PROTEIN AND, AS AN ADJUVANT, A SUBSTANTIALLY NON-IMMUNOGENIC, SEQUENTIALLY HOMOLOGOUS PEPTIDE

The invention relates to a new vaccine comprising a native protein capable of inducing the production of protective antibodies in a host, together with an adjuvant amount of certain proteins or peptides which, as such, are not capable of inducing substantial protective antibody titres but considerably enhance the immunizing activity of said native protein.

More specifically the invention relates to a new picornavirus vaccine comprising inactivated picornavirus and certain adjuvant proteins related to picornavirus.

BACKGROUND OF THE INVENTION

It is known to enhance the effectivity of immunizations by administering the immunogen repeatedly. The second and, if necessary, subsequent booster injections induce high titres of protecting antibodies.

It is also known to enhance the effectivity of an immunogen by a pretreatment of the host with a subunit of the native immunogen. This so-called priming effect has been shown, for example, with a peptide comprising part of the amino acid sequence of the B subunit of cholera toxin. This peptide was coupled to a protein carrier, and the conjugate was used for priming immunizations. After priming, injection with a sub-immunizing amount of cholera toxin led to a substantial level of neutralizing antibodies. [Jacob et al., The EMBO Journal 4 (1985), pages 3339–3343 ].

In case of polio vaccine, Van Wezel et al. [Dev. Biol. Stand. 55 (1984), pages 209–215] have shown a similar priming effect. Injection of poliovirus capsid proteins isolated by means of SDS-PAGE, followed by an injection with inactivated polio vaccine resulted in stimulation of the formation of neutralizing antibodies.

In 1983 Emini et al. [Nature 304 (1983), pages 699–703] have described the priming principle in connection with peptides consisting of 5–10 amino acids coupled to carrier proteins. The sequence of the peptides corresponded with parts of the capsid protein I of type 1 poliovirus (strain: Mahoney). In all cases a stimulation of the neutralizing response to type 1 poliovirus was observed.

Viruses of the picornavirus family are RNA containing viruses. Their diameter is about 30 nm and their protein capsid has the form of an icosaeder.

Based on physico-chemical characteristics the family is divided into four genera:

a. enterovirus (e.g. polio, hepatitis A, echo and coxsackievirus),
b. cardiovirus (e.g. encephalomyocarditis and Mengovirus),
c. rhinovirus and
d. aphtovirus (e.g. foot-and-mouth disease virus).

Within the members of the genera a differentiation into types is made. For example, there are three types (1 to 3) of poliovirus, at least 89 types of rhinovirus and 7 types of foot-and-mouth-diseasevirus.

The poliovirion contains 60 protomers. Each of these protomers consists of four capsid proteins (VP1 to VP4). Capsid proteins VP1, VP2 and VP3 are positioned at the surface of the virion, whereas VP4 is located in the interior of the protein capsid. The position of the three surface positioned capsid proteins is disclosed in Hogle et al. Science 229 (1985), pages 1358–65. The three-dimensional structure of these three capsid proteins is essentially identical. In their native conformation the capsid proteins contain four loops and eight so-called beta-sheets.

The amino acid sequence of the capsid proteins of a number of picornaviruses is known. Picornaviruses having a known primary structure are the three types of poliovirus [Nature 291 (1981), pages 547–553; J. Mol. Biol. 174 (1984), pages 561–585; Proc. Natl. Acad. Sci. USA 81 (1984), pages 1539–1543], hepatitis A (Proc. Natl. Acad. Sci. USA 82 (1985), pages 2627–2631], two types of rhinovirus [Nucl. Ac. Res. 13 (1985) pages 2111–2126; Proc. Natl. Acad. Sci. USA 82 (1985), pages 732–736], coxsackievirus B3 [Vir. Res. 3 (1985), pages 263–270], encephalomyocarditisvirus [Nucl. Ac. Res. 12, (1984) pages 2969–2985], and a number of foot-and-mouth disease virus strains [Gene 17 (1982), pages 153–161; Nucl. Ac. Res. 12 (1984), pages 6587–6601]. Comparison of these sequences shows that the primary structure of the three types of poliovirus is more strongly related to that of the rhinoviruses than to that of hepatitis A. Hepatitis A belongs, just as poliovirus, to the genus of enteroviruses. This shows that the relationship within the genus is not necessarily stronger than that outside the genus. Emini et al. (Virology 140 (1985), pages 13–20) have shown by means of immunochemical techniques that there are relationships between the capsid proteins of a number of enteroviruses and those of rhinovirus 2. Capsid protein 3 showed the strongest cross-reactivity Immunization with inactivated polio vaccine (generally formalin inactivated virus suspension of the three types of poliovirus) results in the formation of neutralizing antibodies. These antibodies bind with the intact virus. The position of the antigenic determinants giving rise to the formation of neutralizing antibodies has been determined by means of the so-called "escape mutans" (Nature 301 (1983), pages 674–679; J. Virol. 57 (1986), pages 246–257). It appears in practically all cases that these determinants occur in the loops of the capsid proteins. The capsid proteins of the poliovirus show a strong mutual interaction. As a consequence of this interaction denaturing conditions have to be used for the isolation of the capsid proteins. Injections with the purified capsid proteins of poliovirus does not result in the formation of significant titres of neutralizing antibodies. This lack of capability to induce the formation of neutralizing antibodies has to be ascribed to the fact that the threedimensional structure of the isolated capsid proteins strongly differs from the threedimensional structure of the proteins in the virus.

Toyoda et al. in J. Mol. Biol. 1984, pages 561–585 disclose the primary structure of the capsid proteins of the three types of poliovirus (of each type the Sabin strain was analyzed). Comparison of these structures shows strong sequential homologies for the three types. The positions in the capsid proteins where differences are observed generally are positioned in the loops of the capsid proteins.

At least two lymphoid cell populations are involved in the formation of antibodies after injection of immunogens: The B cell and the helper T cell. The B cell recognizes the antigenic determinant and the helper cell recognizes the carrier determinant after processing of the immunogen. Eventually, the B cell, after differentiation into a plasma cell, is responsible for the formation of antibodies directed to the antigenic determinant. Based on these immunological data, Gupta et al. (Proc. Natl. Acad. Sci. USA 83 (1986), pages 2604-2608) have suggested that the B cell recognizes the antigenic determinant against which neutralizing antibodies are formed, and that the helper T cell recognizes the rest of the virus. As stated above, the rest of the virus contains a large number of common sequences. The recognition by the helper T cell is considerably less conformation-dependent than the recognition by the B cell. Based on this data and the occurrence of common sequences in native immunogens it seems to be probable that T helper cells recognizing these common structures will be formed after immunization with native proteins or after injection with proteins or peptides showing sequential homology with said native proteins.

The stimulation is observed not only with the virus type homologous with the capsid protein (homotypical), but also for the other virus types (heterotypical). The degree of priming stimulation practically corresponds with that of the booster effect when the vaccine is injected twice. The denatured capsid proteins are not or hardly capable of inducing the formation of neutralizing antibodies. It is believed that this priming stimulation obtained by injection with the carrier portion of an immunogen followed by an injection with the complete immunogen results in stimulation of the antibody response to the hapten (antigenic determinant). Most probably, the common primary structures are responsible for the heterotypical stimulation by the capsid proteins.

DISCUSSION OF THE INVENTION

According to the invention it has been found that immunogenically ineffective proteins and peptides showing sequential homology with a native immunogen do not only show the priming effect when injected some time before vaccination with the native immunogen, but are also useful as adjuvants for said native immunogenic proteins.

The invention is very useful because it provides a vaccine which, by a single vaccination, will induce high titres of neutralizing antibodies with lower doses of native immunogenic protein.

The invention, therefore, provides a vaccine comprising a native protein capable of inducing the production of protective antibodies in a host, together with an adjuvant amount of a protein or peptide showing sequential homology with said native protein but being incapable of effectively inducing the formation of protecting antibodies.

More specifically, the invention provides a picornavirus vaccine comprising as immunogen inactivated picornavirus together with an adjuvant amount of denatured picornavirus capsid protein.

The expression "denatured picornavirus capsid protein" includes proteins isolated from the viral capsid, as well as peptides produced by other methods such as synthetic methods or recombinant DNA techniques insofar as these peptides show sequential homology with the viral capsid proteins. Generally, the denatured picornavirus capsid proteins comprise all of the peptides showing the known priming effect which, as discussed above, is the effect of enhancing the production of neutralizing antibodies by a picornavirus vaccine when the host is injected with the priming peptide some time before the vaccination.

The fact that priming injections or repeated booster vaccinations have now become superfluous is of great advantage to the patient.

It is assumed that the newly found adjuvant effect of the denatured capsid proteins and of the related synthetic peptides is due to an additional stimulation of the T helper cell population involved in the B cell response to the native protein.

Although the invention is illustrated by experimental results obtained with poliovirus, the known presence of identical or similar primary structures in the capsid proteins of viruses as well as the known priming effect occurring with a wide variety of immunogens suggests that the newly found adjuvant effect will be applicable to all kinds of native protein vaccines.

The invention is particularly useful with vaccines comprising inactivated picornavirus, especially inactivated enterovirus, more particularly with enteroviruses selected from the group consisting of inactivated poliovirus, hepatitis A-virus, echovirus, rhinovirus and coxsackievirus.

More specifically, the invention provides vaccines in which the inactivated enterovirus is an inactivated poliovirus selected from the group consisting of poliovirus type 1, poliovirus type 2, poliovirus type 3, and mixtures thereof.

In the vaccines according to the invention it is not necessary for the sequentially homologous proteins or peptides, such as the denatured picornavirus capsid proteins, to be derived from a genus or species idential to that of the native protein used together with the adjuvanting proteins or peptides.

Excellent results have been obtained with a vaccine comprising inactivated poliovirus, such as poliovirus type 1, type 2, type 3 and mixtures thereof, together with denatured poliovirus capsid proteins, viz. VP1, VP2, VP3, VP4 and mixtures thereof. Also in this case, the primary structures of the three types of capsid proteins which are common to all capsid proteins are responsible for the observed heterotypical adjuvant effect upon the neutralizing antibody response to polio vaccine.

The following example is given for illustrative purposes only, and is not to be construed as limiting the invention.

EXAMPLE

Trivalent inactivated polio vaccine

Trivalent inactivated polio vaccine was prepared as described by Van Wezel et al. (Develop. Biol. Stand., 41, 159–168 (1978), Rev. Inf. Dis., 6, 335–340 (1984)) and contained 10, 1, and 6 D-antigen units per ml for the type 1, 2, 3 vaccine components, respectively.

Preparation of a concentrated viral suspension

Type 1 polio virus (Mahoney strain) was cultivated in a microcarrier culture on tertiary monkey kidney cells. The virus harvest was clarified, concentrated and purified according to the methods described in the references mentioned above. The purified virus suspension was concentrated by the addition of 6.3% (w/v) polyethylene glycol. The opalescent suspension was centrifuged (4,000×g; 15 min.) and the pellet was resuspended in M 199 and dialyzed against this medium. The virus suspension was clarified (4,000×g; 15 min.) and the virus was pelleted again (100,000×g; 4 hr.). The pellet was suspended in RBS buffer (composition: 0.01

M Tris, 0.01 M NaCl and 1.5 mM MgCl$_2$, pH 6.0) and its protein content was determined according to the method of Peterson (Anal. Biochem., 83, 346–356 (1977)).

Isolation of capsid proteins i. by HPLC

The isolation of the capsid proteins was done essentially as described by Dernick et al. (Virology 130, 243–246 (1983)). Instead of wide pore C18 silica, wide pore phenyl silica from Vydac (The Separation Groups, Hesparia, California, cat. no. 219) was used. A virus sample containing 1.1 mg virus in 160 μl buffer was mixed with 240 μl formic acid and incubated during five minutes at room temperature. After clarification (10,000 mg;5 min.) a 400 μl sample was injected and the capsid proteins were eluted in 60% (v/v) formic acid with a linear gradient of 60% formic acid in acetonitrile. Fractions containing the capsid proteins were collected. The excess of formic acid and acetonitrile was removed in a speed vacuum concentrator (Savant Inc., Hickville, NY) in combination with an FTS systems Multi Cool (Stone Ridge, NY). Thereafter, the fractions were dialyzed against 8 M urea and analyzed by SDS-PAGE (Nature 227, 680–685(1970)). Finally the protein contents of the fractions were assayed.

ii. by SDS-PAGE

The purified virus suspension was incubated in Laemmli sample buffer (Nature 227, 680–685 (1970)) containing 8 M urea, 2% (w/v) SDS and 0.1 M dithiothreitol during three hours at 37° C. Capsid proteins were isolated by preparative SDS-PAGE in a 3 mm thick 10% slab gel containing 1 M urea. The position of the capsid proteins was localized by covering the gel shortly with a sheet of nitrocellulose and subsequently visualizing protein lines on the sheet by an enzyme immune assay as described by Tonbin et al. (Proc. Natl. Acad. Sci. USA 76, 4350–4354 (1979)). The conjugated antiserum was directed to the denaturated capsid proteins (Vaccine 1, 17–22 (1983)). The capsid proteins were electro-eluted from the cut-out parts of the gel containing the proteins. Their identity was checked by SDS-PAGE, and assay of Peterson was applied for the determination of their protein contents.

Immunization of rats

Four groups consisting of three home-bred spf Wistar rats were injected intramuscularly with a mixture of 30 μg of the separate purified capsid proteins (0.25 ml), trivalent inactivated polio vaccine (injected amount: 2.5, 0.25 and 1.5 D unit for type 1, 2 and 3 components, respectively) and 1.5 mg AlPO$_4$. Five different control groups were injected with the same dose of the four separate purified capsid proteins plus AlPO$_4$ or the same dose of trivalent inactivated polio vaccine plus AlPO$_4$. Blood samples were collected prior and four weeks after injection.

Determination of neutralizing antibodies

The neutralizing antibody titers of the sera were determined in mictrotiter plates by the addition of an infectious polio type 1 (Mahoney strain), type 2 (MEF strain) or type 3 (Saukett strain) virus suspension (100 TCID$_{50}$ for each strain) to a twofold dilution series of the serum samples (50 μl). The serum-virus mixtures were incubated for 24 hours at 37° C. Thereafter $1\times10^4$ Hela cells were added and after five days the 50% neutralization titres were determined.

Results immunization experiment

The neutralization titres of serum samples obtained prior and four weeks after immunization were determined in the neutralization assay. Neither pre-immunization serum samples, nor samples obtained from rats injected with the four capsid proteins only, were able to neutralize the three poliovirus strains tested. The antibody titres of the post-immunization samples of the groups injected with the combinations of capsid proteins and trivalent inactivated polio vaccine in comparison with the controls injected with the same low dose of trivalent vaccine only, are shown in the attached drawing. The results are presented as geometric mean titres and indicate that the addition of all four capsid proteins stimulated the neutralization antibody response with a factor of about 10 to more than 100. In the drawing the figures in parenthesis indicate these stimulation factors. The adjuvant effect of the capsid proteins on the type 3 vaccine component was somewhat behind the effect observed for the type 1 and 2 components.

Essentially the same results were observed with the combination of capsid protein 2 isolated by preparative SDS-PAGE and trivalent inactivated polio vaccine.

We claim:

1. A vaccine comprising an immunogenic protein which induces the production of protective antibodies in a host, and a protein or peptide having sequential homology with said immunogenic protein wherein the protein or peptide having sequential homology will induce the priming effect for said immunogenic protein but which protein or peptide having sequential homology does not induce the formation of protective antibodies to an extent sufficient to confer a protective immunity, the said protein or peptide having sequential homology being present in the vaccine in an amount sufficient to increase the host's response to the immunogenic protein.

2. The vaccine of claim 1 wherein the immunogenic protein is inactivated picornavirus and the protein or peptide having sequential homology is denatured picornavirus capsid protein.

3. The vaccine of claim 2 in which the inactivated picornavirus is an inactivated enterovirus.

4. The vaccine of claim 3 in which the inactivated enterovirus is selected from the group consisting of inactivated poliovirus, hepatitis A virus, echovirus, rhinovirus and coxsackievirus.

5. The vaccine of claim 4 in which the inactivated enterovirus is an inactivated polio virus selected from the group consisting of polio virus type 1, polio virus type 2, polio virus type 3, and mixtures thereof.

6. The vaccine of claim 2, in which the denatured picornavirus capsid protein is derived from a picornavirus genus different from that of the inactivated picornavirus present in the vaccine.

7. The vaccine of claim 2 in which the denatured picornavirus capsid protein is derived from the same picornavirus genus as that of the inactivated picornavirus present in the vaccine.

8. The vaccine of claim 7 in which the inactivated picornavirus is an inactivated enterovirus and the denatured picornavirus capsid protein is a denatured enterovirus capsid protein.

9. The vaccine of claim 8 in which the inactivated enterovirus is inactivated poliovirus, and the denatured enterovirus capsid protein is denatured poliovirus capsid protein.

10. The vaccine of claim 9 in which the denatured poliovirus capsid protein is selected from the group consisting of VP1, VP2, VP3, VP4, and mixtures thereof.

11. The vaccine of claim 9 in which the inactivated poliovirus is selected from the group consisting of inactivated poliovirus type 1, type 2, type 3, and mixtures thereof.

* * * * *